(12) United States Patent
Ghelmansarai

(10) Patent No.: US 6,925,149 B2
(45) Date of Patent: Aug. 2, 2005

(54) RADIATION IMAGING SYSTEM

(75) Inventor: Farhad A. Ghelmansarai, Danville, CA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 365 days.

(21) Appl. No.: 10/209,521

(22) Filed: Jul. 30, 2002

(65) Prior Publication Data

US 2004/0022357 A1 Feb. 5, 2004

(51) Int. Cl.$^7$ ............................................. H05G 1/08
(52) U.S. Cl. ........................ 378/98.2; 378/98; 378/91
(58) Field of Search .............................. 378/64, 65, 98, 378/98.2, 98.3, 91; 250/361 R, 363.01, 363.02, 363.09; 348/207.99, 362, 370, 371

(56) References Cited

U.S. PATENT DOCUMENTS

| | | | |
|---|---|---|---|
| 5,600,701 A | * | 2/1997 | Baba et al. ................. 378/98.2 |
| 6,052,432 A | | 4/2000 | Rieppo et al. |
| 6,222,544 B1 | * | 4/2001 | Tarr et al. .................... 345/839 |
| 6,463,121 B1 | * | 10/2002 | Milnes ....................... 378/98.2 |

OTHER PUBLICATIONS

Siemens, "TV Block diagram", download from http://training.sms.siemens.com/tech/tests/RX1RSBASICSA/selfstdy/chapters/tv/pick_up.htm on Jun. 13, 2002—27 pages.
MAtrox Imaging Tutorial, "Camera Interface Guide" Jan. 11, 1996.

* cited by examiner

Primary Examiner—Edward J. Glick
Assistant Examiner—Chih-Cheng Glen Kao
(74) Attorney, Agent, or Firm—Siemens Corporation

(57) ABSTRACT

A system for capturing an image of transmitted radiation includes transmission of a disable signal to disable a bias light of a camera at a time prior to transmission of radiation, and acquisition of an image from the camera during transmission of the radiation and during deactivation of the bias light. In some embodiments, the disable signal is transmitted in response to the reception of a pre-radiation signal, the pre-radiation signal indicating that transmission of the radiation will commence approximately one frame scan time after the pre-radiation signal is received, and the disable signal is transmitted approximately when the pre-radiation signal is received.

23 Claims, 5 Drawing Sheets

RADIATION IMAGING SYSTEM

BACKGROUND

1. Field

The present invention relates generally to radiation imaging, and more particularly to systems used to acquire radiation images.

2. Description

Conventional radiation treatment typically involves directing a radiation beam at a tumor in a patient to deliver a predetermined dose of treatment radiation to the tumor according to an established treatment plan. A suitable radiation treatment device is described in U.S. Pat. No. 5,668, 847, issued Sep. 16, 1997 to Hernandez, the contents of which are incorporated herein for all purposes.

Healthy tissue and organs are often in the treatment path of the radiation beam during radiation treatment. The healthy tissue and organs must be taken into account when delivering a dose of radiation to the tumor, thereby complicating determination of the treatment plan. Specifically, the plan must strike a balance between the need to minimize damage to healthy tissue and organs and the need to ensure that the tumor receives an adequately high dose of radiation. In this regard, cure rates for many tumors are a sensitive function of the radiation dose they receive.

Treatment plans are therefore designed to maximize radiation delivered to a target while minimizing radiation delivered to healthy tissue. If the radiation is not delivered exactly as required by the treatment plan, the goals of maximizing target radiation and minimizing healthy tissue radiation may not be achieved. More specifically, errors in radiation delivery can result in low irradiation of tumors and high irradiation of sensitive healthy tissue. The potential for mis-irradiation increases with increased delivery errors.

Many types of systems have been developed to ensure that radiation will be delivered to a proper area and with the proper dosage. For example, a light field is often used to indicate the position of a field within which radiation will be delivered. Accordingly, these systems rely on various techniques to ensure that the light field and the field of actually-delivered radiation are congruent. Some of these techniques verify the congruence using images obtained by portal imaging devices.

Modern radiation therapy uses beam-shaping devices to produce radiation fields of various shapes. These radiation fields may be used to provide more precise treatment than otherwise available. In order to avoid irradiation of unintended targets by a shaped radiation field, an operator verifies that the beam-shaping devices are configured so as to produce a field shape that complies with a specified treatment plan. As described above, this verification often includes the comparison and manipulation of images obtained by a portal imaging device.

In addition, the accuracy of some techniques for verifying an applied radiation dosage increases with the sensitivity to radiation of an imaging device that is used in conjunction with the techniques. Accordingly, it would therefore be beneficial to provide a radiation imaging system that may offer more efficient and accurate verification of field congruence, field shape, and/or radiation dosage. When used in conjunction with conventionally-designed treatments, such a system could reduce the chance of harming healthy tissue. Such system may therefore also allow the use of more aggressive treatments than currently available.

SUMMARY

To address at least the above problems, some embodiments of the present invention provide a system, method, apparatus, and means to transmit a disable signal to disable a bias light of a camera at a time prior to transmission of radiation, and to acquire an image from the camera during transmission of the radiation and during deactivation of the bias light. In some aspects of these embodiments, the disable signal is transmitted in response to the reception of a pre-radiation signal, the pre-radiation signal indicating that transmission of the radiation will commence approximately one frame scan time after the pre-radiation signal is received, and the disable signal is transmitted approximately when the pre-radiation signal is received.

According to some embodiments, the present invention provides a linear accelerator to emit radiation, a camera to acquire image data representing the emitted radiation, and a device to transmit a disable signal to disable a bias light of the camera at a time prior to emission of the radiation, wherein the camera acquires image data during transmission of the radiation and during deactivation of the bias light.

The present invention is not limited to the disclosed embodiments, however, as those of ordinary skill in the art can readily adapt the teachings of the present invention to create other embodiments and applications.

BRIEF DESCRIPTION OF THE DRAWINGS

The nature of this invention, as well as its advantages, will become readily apparent from consideration of the following specification as illustrated in the accompanying drawings, in which like reference numerals designate like parts, and wherein.

DETAILED DESCRIPTION

The following description is provided to enable any person of ordinary skill in the art to make and use the invention and sets forth the best modes contemplated by the inventor for carrying out the invention. Various modifications, however, will remain readily apparent to those in the art.

Figure 1:
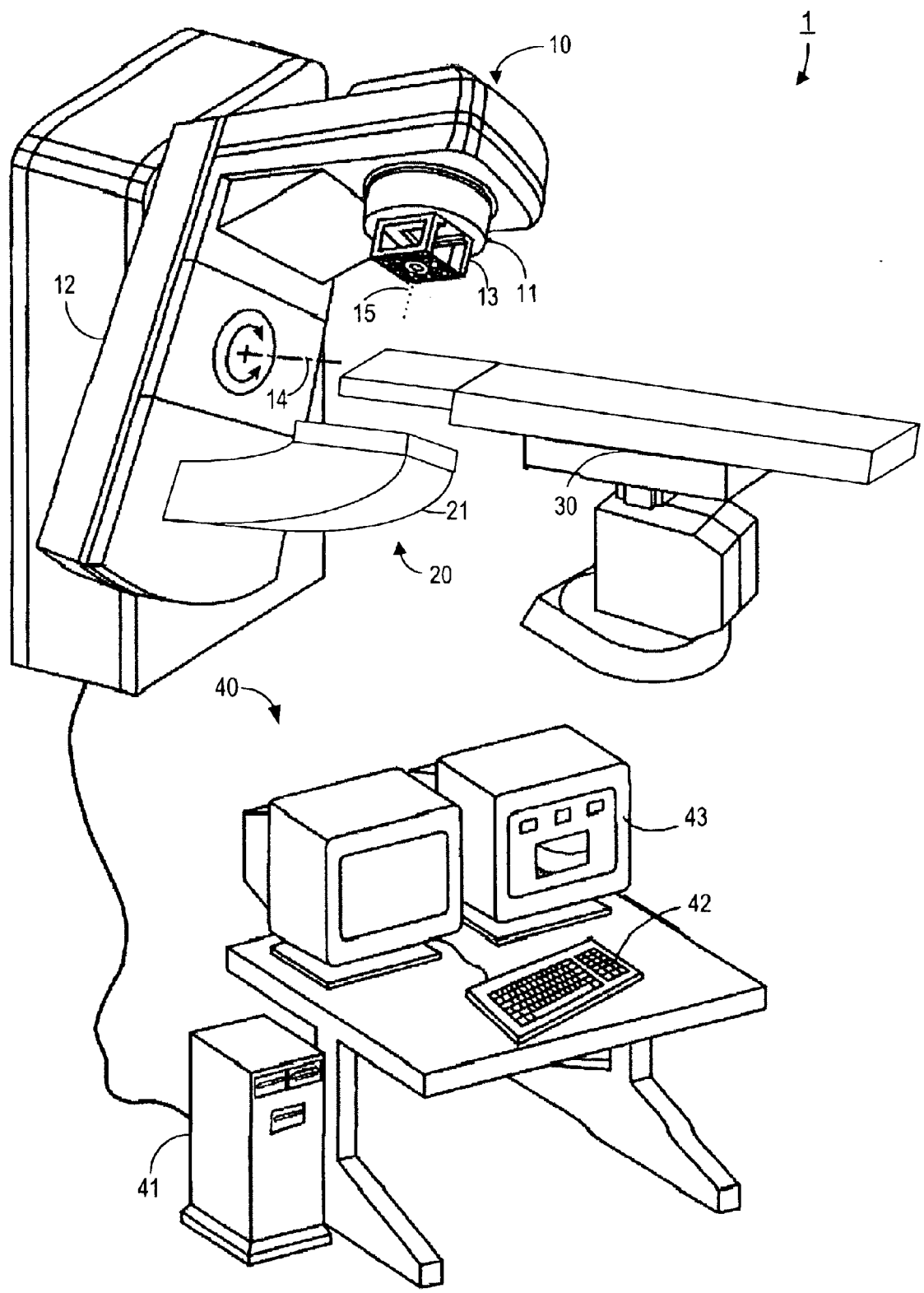
FIG. 1 is diagram illustrating a radiation treatment room according to some embodiments of the present invention.

FIG. 1 illustrates radiation treatment room 1 pursuant to some embodiments of the present invention. Radiation treatment room 1 includes linear accelerator (linac) 10, imaging device 20, treatment table 30 and operator station 40. The elements of radiation treatment room 1 are used to deliver treatment radiation to a patient according to a radiation treatment plan.

Linac 10 delivers treatment radiation to a treatment area and is primarily composed of treatment head 11 and gantry 12. Accessory tray 13 is mounted on treatment head 11 and may be configured to receive and securely hold attachments used during the course of treatment planning and treatment (such as, for example, reticles, wedges, or the like). Treatment head 11 also includes a beam-emitting device for emitting treatment radiation and a beam-shielding device, or collimator, for shaping the radiation and for shielding sensitive surfaces therefrom. The treatment radiation may comprise electron, photon or any other type of radiation.

Treatment head also includes a light-emitting device such as a light bulb. The light bulb is used as described above to produce a light field that is used to confirm a location of a radiation field to be delivered. In this regard, the term "light" will be used to describe the radiation emitted from the light bulb and used to produce a light field. On the other hand, the terms "treatment radiation" and "radiation" will be used herein to identify radiation emitted by the beam-emitting device and used to treat a patient.

Treatment head 11 is fastened to a projection of gantry 12. Gantry 12 is rotatable around axis 14 before, during and after radiation treatment. During such treatment, radiation is delivered from linac 10 to the beam-emitting device of treatment head 11 and emitted therefrom along beam path 15. The delivered radiation is focused on a point, known as the isocenter, which is located at the intersection of beam path 15 and axis 14. Due to divergence of the emitted radiation and shaping of the radiation by the collimator leaves, the radiation is delivered to a radiation field rather than only to the point upon which the radiation is focused.

Imaging device 20 acquires images that are used before, during and after radiation treatment. More particularly, imaging device 20 is used to acquire images for verification and recordation of a patient position, a collimator position, a treatment dosage, and an internal patient portal to which radiation is to be delivered. These images are used to ascertain whether each of these variables conform to a desired treatment plan.

In some embodiments, imaging device 20 comprises light-proof housing 21 within which are disposed a scintillator and a tube-based camera. Generally, imaging device 20 may be used to acquire images of items irradiated by light and/or treatment radiation. Housing 21 may be attached to gantry 12 in any manner, and may include an extendible and retractable structure. Pursuant to some embodiments of the present invention, this structure may be used to advance and retract imaging device 20 to and from an imaging position along beam path 15 in order to acquire images required for treatment. According to some embodiments, imaging device 20 comprises the BEAMVIEW™ system produced by the present assignee. Further details of the structure and operation of imaging device 20 according to some embodiments of the invention are set forth below with respect to FIG. 2.

Table 30 supports a patient during radiation treatment. Table 30 is adjustable to ensure, along with rotation of gantry 12, that an area of the patient that is to be treated is positioned at the isocenter.

Operator station 40 includes a processor 41 in communication with an input device such as keyboard 42 and an operator console 43 (including one or more visual display units or monitor). Operator station 40 is typically operated by an operator who administers actual delivery of radiation treatment as prescribed by an oncologist. The operator uses keyboard 42 to perform calibration procedures including verification of field congruence and acquisition of data used for image correction, to input data defining a radiation dose to be delivered to the patient, and to deliver treatment radiation to the patient. The data may also be input via another input device, such as a data storage device. Operator console 42 displays data to the operator before, during and after the treatment.

Operator station 40 may be located apart from linac 10, such as in a different room, in order to protect the operator from radiation. For example, linac 10 may be located in a heavily shielded room, such as a concrete vault, which shields the operator from radiation generated by linac 10.

Processor 41 may store processor-executable process steps according to some embodiments of the present invention. In some embodiments, the process steps are executed by processor 41, linac 10, imaging device 20, and/or another device to transmit a disable signal to disable a bias light of a camera at a time prior to transmission of radiation, and to acquire an image from the camera during transmission of the radiation and during deactivation of the bias light. In some aspects of these embodiments, the disable signal is transmitted in response to the reception of a pre-radiation signal, the pre-radiation signal indicating that transmission of the radiation will commence approximately one frame scan time after the pre-radiation signal is received, and the disable signal is transmitted approximately when the pre-radiation signal is received.

The above-described steps may also be embodied, in whole or in part, by hardware of processor 41, linac 10, imaging device 20. Moreover, embodiments of the invention may be embodied by hardware and/or software of a standalone device connected between imaging device 20 and operator station 40, between linac 10 and imaging device 20, or elsewhere.

Of course, each of the devices shown in FIG. 1 may include less or more elements than those shown. Moreover, transformation and storage of acquired data may be performed by any one or more of the devices. In addition, embodiments of the invention are not limited to the devices shown.

Figure 2:
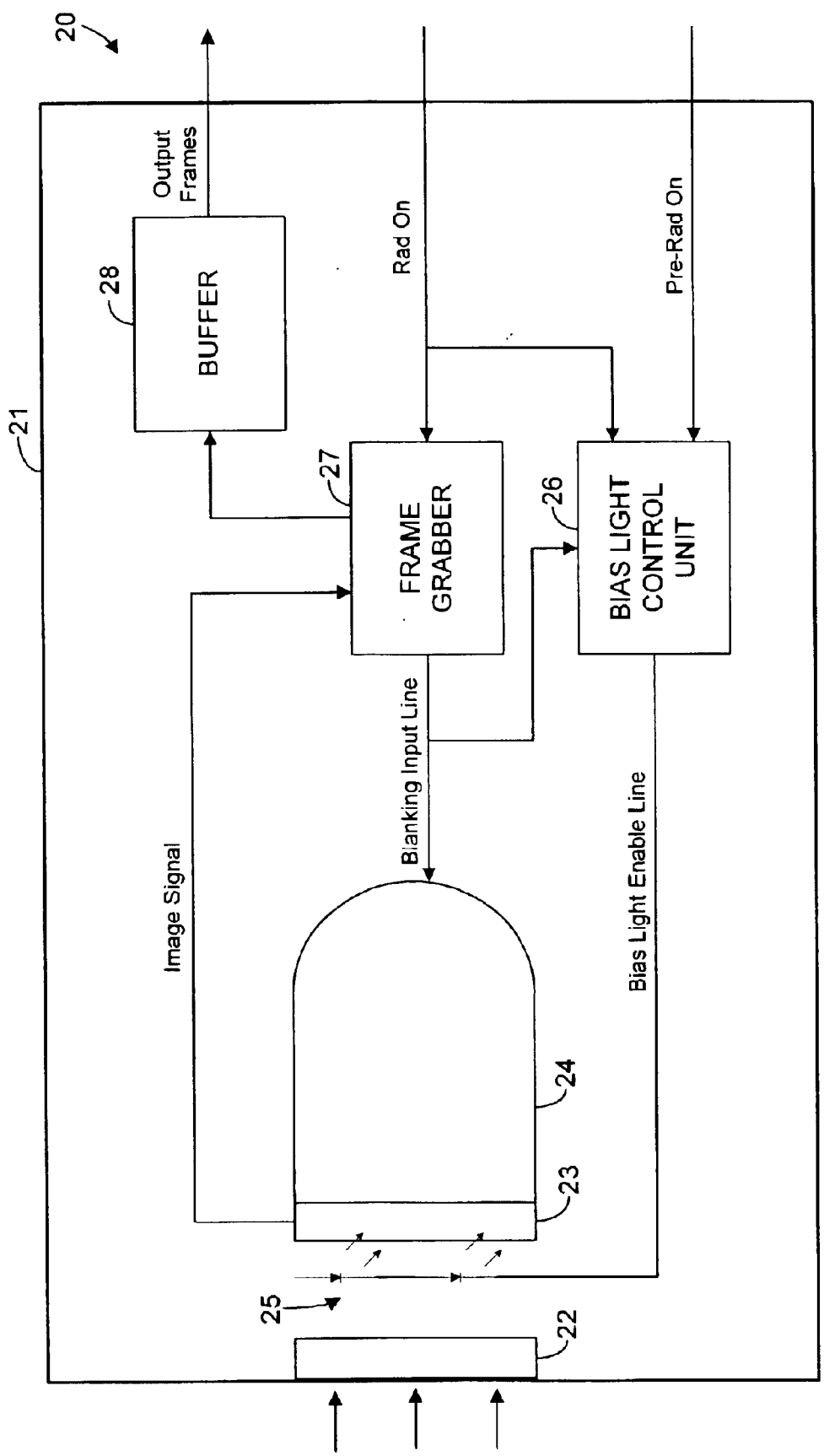
FIG. 2 is a diagram illustrating elements of a camera according to some embodiments of the present invention.

FIG. 2 is a diagram illustrating several elements of imaging device 20 according to some embodiments of the invention. It should be noted that the diagram is intended to represent functional relationships of the elements according to some embodiments and does not necessarily portray actual physical relationships or sizes. In addition, it is contemplated that imaging device 20 may include more or less elements than shown in FIG. 2.

As shown, imaging device 20 and housing 21 include scintillator 22, which is composed of cesium-iodide scintillator material in some embodiments but may also be composed of other materials. One possible material is gadolinium-oxisulfide, which exhibits a poorer contrast transfer function and greater optical scattering than cesium-iodide. By virtue of its composition, scintillator 22 absorbs treatment radiation emitted from treatment head 11 and emits visible photons having intensity proportional to that of the absorbed radiation toward target 23. In some embodiments, one or more optical devices such as mirrors, lenses and fiber-optic bundles are placed between scintillator 22 and target 23. Accordingly, scintillator 22 and target 23 need not be linearly aligned as shown in FIG. 2.

Target 23 comprises a plate containing an optical-sensing material that generates electrons in proportion to an amount of light it absorbs. Therefore, the material of target 23 reacts in proportion to an amount of radiation absorbed by scintillator 22. Target 23 is an element of camera tube 24, which also includes elements for generating and scanning an electron beam across target 23. Upon striking target 23, target 23 gives off an amount of electrons that is proportional to the amount of light absorbed by target 23. These electrons comprise an image signal that represents any object that is not completely transparent to the treatment radiation and that is placed between treatment head 11 and scintillator 22. In some embodiments, target 23, camera tube 24 are elements of a high-resolution 1 k×1 k Saticon™ camera that operates in progressive mode.

Bias lights 25 are positioned so as to illuminate target 23. Although bias lights 25 of FIG. 2 appear to be positioned so as to prevent photons emitted by scintillator 22 from hitting target 23, it should be noted that in some embodiments bias lights 25 are positioned to avoid this phenomenon.

Bias lights 25 are intended to compensate for negative charges that build up in target 23 when scanned by the electron beam under dark conditions. The time required for this compensation is known as the buildup lag of tube 24. Bias lights 25 may comprise one or more light-emitting diodes and/or other light sources, and are controlled by a bias light enable signal transmitted by bias light control unit 26 in accordance with some embodiments of the present invention. This control is described in detail with respect to FIG. 3.

The image signal output from target 23 is received by frame grabber 27, which digitizes the signal and produces still frames therefrom. In some embodiments, frame grabber 27 uses 12-bit processing to improve the dynamic range of imaging device 20. Frame grabber 27 may produce still frames in conjunction with buffer 28, and/or may include its own buffer. Although shown as elements of imaging device 20 and contained within housing 21, it should be noted that one or more of bias light control unit 26, frame grabber 27 and buffer 28 may not be included in imaging device 20 and/or within housing 21.

Generally, camera tube 24 is capable in some embodiments of target integration. During target integration, a blanking input is transmitted to camera 24 for a specified integration period. During this period, an electron beam of camera 24 does not scan target 23 and therefore no image signal is produced by target 23. After the integration period, the electron beam scans target 23 and the magnitude of the electrical signal produced thereby is proportional to a number of photons that had impacted target 23 during the integration period.

For purposes of the foregoing description of some embodiments, it should be noted that camera tube 24 also produces its own horizontal blanking and vertical blanking pulses. The horizontal blanking pulse is produced to turn off the electron beam while it is being repositioned at the beginning of a next horizontal scan line, and the vertical blanking pulse is produced to turn off the electron beam while it is being repositioned at the top of the frame. When the blanking input signal from frame grabber 27 is enabled, the electron beam continues to scan target 23 until a next vertical blanking pulse is received. Similarly, when the blanking input signal is disabled, the electron beam remains off until a next vertical blanking pulse.

Enabling and disabling of the blanking input according to some embodiments of the invention is based on a Rad On signal produced by linac 10 and received by bias light control unit 26 and frame grabber 27, and on a Pre-Rad On signal produced by linac 10 and received by bias light control unit 26. The Rad On signal is an electrical signal indicating that treatment radiation is being transmitted. The Pre-Rad On signal indicates a start time at which transmission of the radiation will commence. In some embodiments, the start time is one frame scan time after receipt of the Pre-Rad On signal.

According to some embodiments, bias light control unit 26 transmits a signal to disable bias lights 25 approximately upon receipt of the Pre-Rad On signal. In a case that the start time is one frame scan time after receipt of the Pre-Rad On signal, bias lights 25 will therefore be disabled one frame scan time prior to commencement of the treatment. The present inventor has discovered that disabling bias lights 25 in this manner allows for more accurate dosimetric measurements.

Figure 3:
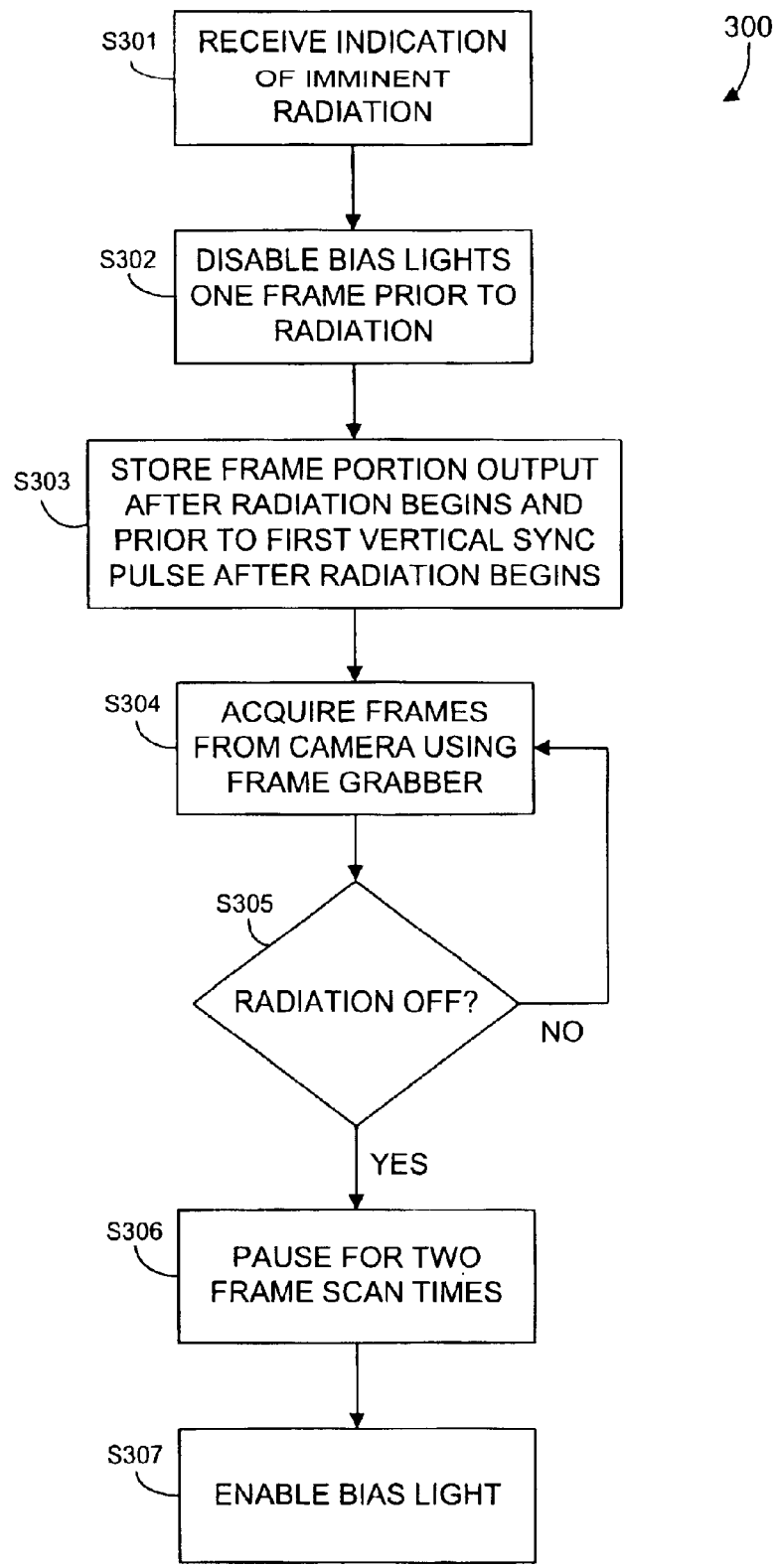
FIG. 3 is a flow diagram illustrating process steps according to some embodiments of the present invention.

FIG. 3 is a flow diagram of process steps 300 according to some embodiments of the invention. Process steps 300 may be embodied by hardware and/or software of processor 41, linac 10, imaging device 20, bias light control unit 26 and/or another device in direct or indirect communication with bias lights 25.

Initially, in step S301, an indication of imminent radiation is received. According to the present example, the indication is received by bias light control unit 26 in the form of a Pre-Rad On signal transmitted by linac 10. The Pre-Rad On signal is transmitted by linac 10 at a time prior to transmission of treatment radiation, and indicates a start time at which the transmission will commence. In some embodiments, the start time is approximately one frame scan time after the Pre-Rad On signal is received.

Bias lights 25 are disabled in step S302. Bias lights 25 may be disabled in response to reception of the Pre-Rad On signal, and/or at a specific disable time. The disable time may be related to the start time indicated by the Pre-Rad On signal. For example, bias lights 25 may be disabled substantially immediately upon receipt of the Pre-Rad On signal, wherein the Pre-Rad On signal indicates that treatment radiation will be transmitted approximately one frame scan time after receipt of the Pre-Rad On signal. Therefore, bias lights 25 are disabled approximately one frame scan time prior to transmission of the radiation. Of course, bias lights 25 may be disabled based on a different temporal relationship with the Pre-Rad On signal and/or the commencement of radiation transmission.

Bias lights 25 may be disabled in many ways. In one example, bias light control unit 26 transmits a "low" signal on the bias light enable line and bias lights 25 are turned off in response to the signal. Bias lights 25 may also be disabled by causing a physical obstruction to be placed between bias lights 25 and target 23 such that target 23 is minimally exposed to photons emitted by bias lights 25.

Figure 4:
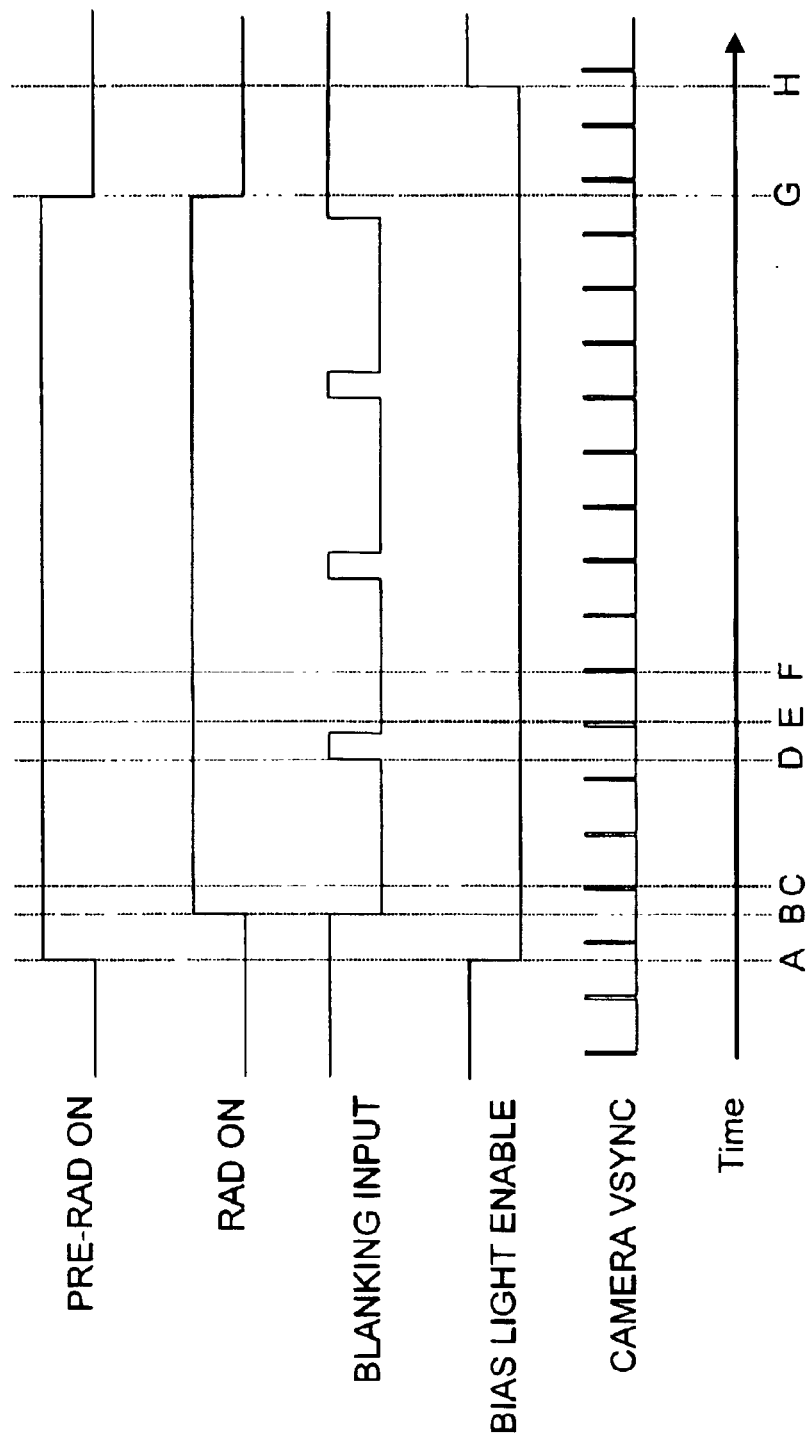
FIG. 4 is a waveform timing diagram according to some embodiments of the present invention.

Next, in step S303, a portion of a frame is stored after transmission of the treatment radiation commences. The stored portion represents a portion of target 23 that is scanned by an electron beam after the transmission commences and prior to a first vertical sync pulse of camera tube 24. FIG. 4 is a timing diagram that will be used to explain some embodiments of step S303.

FIG. 4 shows the Pre-Rad On signal being received in step S301 at time A. In response to the received signal, the bias light control unit 26 transmits an inactive (low) signal on the bias light enable line in step S302. The Rad On signal goes active (high) at time B, which is one frame scan time after reception of the Pre-Rad On signal (time A). As a result, bias lights 25 are disabled one frame scan time prior to the transmission of radiation. In this regard, one frame scan time is defined as the distance between subsequent pulses of the camera Vsync signal.

The Rad On signal transmitted by linac 10 is received by frame grabber 27. Frame grabber 27 transmits an active signal to the blanking input of camera tube 24 in response to the Rad On signal at time B. It should be noted that the blanking signal is active low according to the present example. Accordingly, a low blanking signal comprises an indication to turn off the electron beam of camera tube 24. It should also be noted that although state changes of the Pre-Rad On signal and the bias light enable signal are described as occurring at time A and state changes of the Rad On signal and the blanking input signal are described as occurring at time B, these state changes do not occur simultaneously according to some embodiments.

The blanking signal is received by camera tube 24 at time B, but the electron beam does not turn off until time C. This delay is due to the operation of camera 24 of the present example, in which a blanking signal received during a frame scan is ignored until a next vertical synchronization pulse is issued. The electron beam therefore scans target 23 during a time period between time B and time C, resulting in an image signal that is stored by frame grabber 27 in step S303.

In some embodiments, image frames are then acquired in step S304 according to conventional operation of imaging device 20. Frame grabber therefore deactivates the blanking input signal after a specified integration time has elapsed. The integration time is depicted in FIG. 4 as the period between time C and time D. Once the blanking signal is deactivated, the electron beam begins scanning target 23 after a next camera Vsync pulse. For example, deactivation of the blanking input signal at time D results in a frame scan beginning at time E. The frame scan, which lasts from time E to time F, results in the generation and acquisition of an image frame representing the treatment radiation transmitted between time C and time E, as well as some of the radiation transmitted between time E and F. The remaining radiation transmitted between time E and F is represented in a subsequently-generated image frame.

Frames are acquired in this manner in step S304 until it is determined in step S305 that transmission of the treatment radiation has stopped. In one example, bias light control unit 26 determines that the transmission has stopped by detecting that Rad On signal has gone inactive. According to FIG. 4, this determination is positive at time G and flow therefore proceeds to step S306.

Process steps 300 pause for two frame scans at step S306. Two frame scan times are used to ensure that bias lights 25 are not enabled during the final frame scan. In more detail, the Rad On signal may go inactive during a camera Vsync pulse. In response to the inactive Rad On signal, frame grabber 27 transmits an inactive blanking input signal. However, the electron beam of camera tube 24 will not turn on until a next Vsync pulse, which is approximately one frame scan time from the stoppage of radiation. Moreover, the final frame scan that begins after the next Vsync pulse will not finish until after an additional frame scan time elapses. Therefore, bias lights 25 are then enabled in step S307 at time H, which is two frame scan times after time G.

Figure 5:
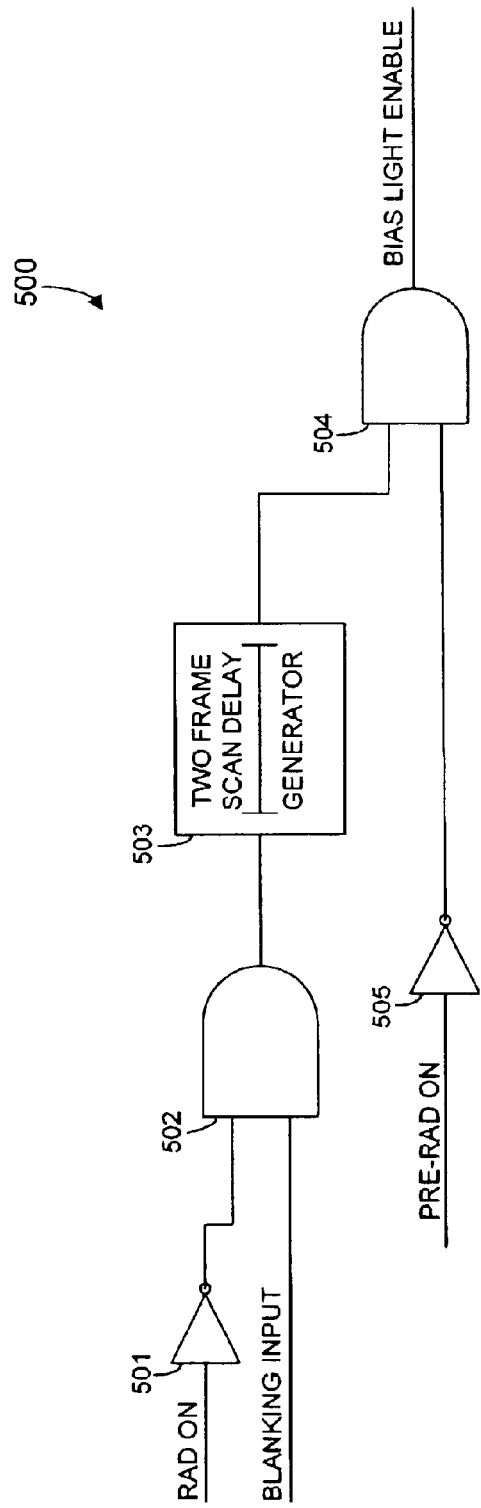
FIG. 5 is a logic circuit diagram according to some embodiments of the present invention.

FIG. 5 shows a functional logic diagram of circuit 500 for implementing process steps 300 according to some embodiments of the invention. Particularly, elements 501 through 505 use the Rad On and the Pre-Rad On signals from linac 10 and the blanking input signal from frame grabber 27 to produce a bias light enable signal having a timing according to some embodiments of the present invention. Circuit 500 may be embodied in bias light control unit 26 and/or in one or more other devices.

Other hardware and/or software elements may be used to improve the performance of a radiation imaging system according to some embodiments of the present invention. For example, acquired images may be corrected to decrease any inherent shading using hardware-based shading correction. Shading is often defined as a variation in amplitude of an output video signal while the imaging device is uniformly illuminated. Shading correction may involve dynamically regulating the electron beam current in camera tube 24. More specifically, a parabolic voltage is used to modulate a potential of a cathode of tube 24. This potential controls the electron beam current in synchrony with the scanning of target 23 by the electron beam in order to provide the shading correction.

Benefits provided by one or more of shading correction, bias light control, and optical scattering reduction allow a radiation imaging system according to some embodiments of the present invention to perform accurate dosimetric measurements. Moreover, a radiation system according to some embodiments of the present invention may be used to correct geometric distortions and verify collimator leaf positions using currently- or hereafter-known techniques.

In order to correct geometric distortions in treatment doses, an extent of the distortion is determined by acquiring an image of a known test pattern, such as a rectangular array of spots. The position of each spot in the acquired image is compared to its position in the known, undistorted pattern to produce a mapping that describes the geometric distortion. Geometric distortion may also be corrected by creating a mathematical model of the system as a function of distortion effects caused by each element of the system, or by modulating the sweep of the electron beam as described above.

A collimator leaf position may be verified by placing an accessory in treatment head 11 that causes the leaves to form a known configuration. A light field is defined by the leaves and compared with a drawing of an expected light field that is attached to treatment head 11. The leaves are then adjusted so that the defined light field matches the expected light field. A reference radiation image is then acquired using imaging device 20. Later, an operator attempts to place the leaves so as to again define the expected light field. To verify that the re-configured leaves define the expected light field, a radiation image is acquired, an edge detection algorithm is applied to the radiation image and to the reference radiation image, the edge-corrected images are subtracted from one another, and any deviation is identified in numbers of pixels using image analysis tools. Since the dimensions representing each pixel at the collimator are known, the deviation may be converted from numbers of pixels to units of length.

Using some embodiments of the present invention, one or more of the foregoing correction and verification techniques will be more effective than previously available because the resolution and/or accuracy of acquired images will be better than previously available.

Those in the art will appreciate that various adaptations and modifications of the above-described embodiments can be configured without departing from the scope and spirit of the invention. For example, the particular arrangement of process steps 300 is not meant to imply a fixed order to the steps; embodiments of the present invention can be practiced in any order that is practicable. Therefore, it is to be understood that, within the scope of the appended claims, the invention may be practiced other than as specifically described herein.

What is claimed is:

1. A method for capturing an image, comprising: transmitting a disable signal to disable a bias light of a camera at a time prior to transmission of radiation;
   transmitting a first vertical synchronization pulse comprising an instruction to disable an electron beam of the camera;
   detecting commencement of the transmission of radiation after transmitting the first vertical synchronization pulse and prior to transmitting a next vertical synchronization pulse;

after detecting the commencement and prior to transmitting the next vertical synchronization pulse, operating the electron beam to acquire an image during the transmission of the radiation and during disabling of the bias light, the acquired image representing first radiation received by the camera after the commencement and prior to transmission of the next vertical synchronization pulse;

transmitting the next vertical synchronization pulse; and disabling the electron beam in response to the next vertical synchronization pulse.

2. A method according to claim 1, wherein the time is based on a frame scan time of the camera.

3. A method according to claim 2, wherein the time is approximately equal to the frame scan time of the camera.

4. A method according to claim 1, further comprising:

receiving a pre-radiation signal, the pre-radiation signal indicating a start time at which transmission of the radiation will commence, wherein the disable signal is transmitted in response to the reception of the pre-radiation signal.

5. A method according to claim 4, wherein the disable signal is transmitted at a disable time, the disable time being based on the start time and on a frame scan time of the camera.

6. A method according to claim 5, wherein the disable time is approximately one frame scan time before the start time.

7. A method according to claim 4, wherein a frame scan time is associated with the camera, wherein the start time is approximately one frame scan time after the pre-radiation signal is received, and wherein the disable signal is transmitted approximately when the pre-radiation signal is received.

8. A method according to claim 1, further comprising:

receiving an indication that transmission of the radiation has stopped; and transmitting an enable signal to enable the bias light at least two frame scan times after the radiation has stopped.

9. A computer-readable medium storing processor-executable process steps, the process steps comprising: a step to transmit a disable signal to disable a bias light of a camera at a time prior to transmission of radiation;

a step to transmit a first vertical synchronization pulse comprising an instruction to disable an electron beam of the camera;

a step to detect commencement of the transmission of radiation after transmitting the first vertical synchronization pulse and prior to transmitting a next vertical synchronization pulse;

a step to operate the electron beam to acquire, after detecting the commencement and prior to transmitting the next vertical synchronization pulse, an image during the transmission of the radiation and during disabling of the bias light, the acquired image representing first radiation received by the camera after the commencement and prior to transmission of the next vertical synchronization pulse;

a step to transmit the next vertical synchronization pulse; and a step to disable the electron beam in response to the next vertical synchronization pulse.

10. A medium according to claim 9, wherein the time is approximately equal to a frame scan time of the camera.

11. A medium according to claim 9, the process steps further comprising:

a step to receive a pre-radiation signal, the pre-radiation signal indicating a start time at which transmission of the radiation will commence, wherein the disable signal is transmitted in response to the reception of the pre-radiation signal.

12. A medium according to claim 11, wherein a frame scan time is associated with the camera, wherein the start time is approximately one frame scan time after the pre-radiation signal is received, and wherein the disable signal as transmitted approximately when the pre-radiation signal is received.

13. A medium according to claim 9, the process steps further comprising:

a step to receive an indication that transmission of the radiation has stopped; and a step to transmit an enable signal to enable the bias light at least two frame scan times after the radiation has stopped.

14. A device comprising:

at least one memory storing processor-executable process steps;

at least one processor in communication with the at least one memory and operative in conjunction with the stored process steps to:

transmit a disable signal to disable a bias light of a camera at a time prior to transmission of radiation;

transmit a first vertical synchronization pulse comprising an instruction to disable an electron beam of the camera;

detect commencement of the transmission of radiation after transmitting the first vertical synchronization pulse and prior to transmitting a next vertical synchronization pulse;

operate the electron beam to acquire, after detecting the commencement and prior to transmitting the next vertical synchronization pulse, an image during the transmission of the radiation and during disabling of the bias light, the acquired image representing first radiation received by the camera after the commencement and prior to transmission of the next vertical synchronization pulse;

transmit the next vertical synchronization pulse; and disable the electron beam in response to the next vertical synchronization pulse.

15. A device according to claim 14, wherein the time is approximately equal to a frame scan time of the camera.

16. A device according to claim 15, the processor further operative in conjunction with the stored process steps to:

receive a pre-radiation signal, the pre-radiation signal indicating a start time at which transmission of the radiation will commence, wherein the disable signal is transmitted in response to the reception of the pre-radiation signal.

17. A device according to claim 16, wherein a frame scan time is associated with the camera, wherein the start time is approximately one frame scan time after the pre-radiation signal is received, and wherein the disable signal is transmitted approximately when the pre-radiation signal is received.

18. A device according to claim 14, the processor further operative in conjunction with the stored process steps to:

receive an indication that transmission of the radiation has stopped; and transmit an enable signal to enable the bias light at least two frame scan times after the radiation has stopped.

19. A system comprising:

a linear accelerator to emit radiation;

a camera to transmit a first vertical synchronization pulse comprising an instruction to disable an electron beam of the camera, to detect commencement of transmission of radiation after transmitting the first vertical synchronization pulse and prior to transmitting a next vertical synchronization pulse, to operate the electron beam to acquire, after detecting the commencement and prior to transmitting a next vertical synchronization pulse, an image during the transmission of the radiation and during disabling of a bias light, the acquired image representing first radiation received by the camera after the commencement and prior to transmission of the next vertical synchronization pulse, to transmit the next vertical synchronization pulse, and to disable the electron beam in response to the next vertical synchronization pulse; and a device to transmit a disable signal to disable the bias light of the camera at a time prior to emission of the radiation.

20. A system according to claim 19, wherein the time is approximately equal to a frame scan time of the camera.

21. A system according to claim 19, wherein the device receives a pre-radiation signal from the linear accelerator, the pre-radiation signal indicating a start time at which transmission of the radiation will commence, and wherein the device transmits the disable signal in response to the reception of the pre-radiation signal.

22. A system according to claim 21, wherein a frame scan time is associated with the camera, wherein the start time is approximately one frame scan time after the pre-radiation signal is received, and wherein the disable signal is transmitted approximately when the pre-radiation signal is received.

23. A system according to claim 19, wherein the device receives an indication that the linear accelerator has stopped emitting radiation, and transmitted an enable signal to enable the bias light at least two frame scan times after the linear accelerator has stopped.

* * * * *